US011472088B1

(12) United States Patent
Domenick et al.

(10) Patent No.: US 11,472,088 B1
(45) Date of Patent: Oct. 18, 2022

(54) SYSTEM AND METHOD FOR MANUFACTURING A COSMETIC STICK

(71) Applicant: Kolmar Laboratories, Inc., Port Jervis, NY (US)

(72) Inventors: Vincent Domenick, New Paltz, NY (US); Cheryl Ewing, Port Jervis, NY (US); Matt Abbadessa, Sparrowbush, NY (US)

(73) Assignee: PORT JERVIS LABORATORIES, INC., Port Jervis, NY (US)

( * ) Notice: Subject to any disclaimer, the term of this patent is extended or adjusted under 35 U.S.C. 154(b) by 845 days.

(21) Appl. No.: 16/212,031

(22) Filed: Dec. 6, 2018

Related U.S. Application Data

(62) Division of application No. 15/231,230, filed on Aug. 8, 2016, now Pat. No. 10,183,433.

(51) Int. Cl.
| | | |
|---|---|---|
| *B29C 48/275* | (2019.01) | |
| *B29C 48/17* | (2019.01) | |
| *B29C 48/21* | (2019.01) | |
| *B29C 39/12* | (2006.01) | |
| *B29C 39/02* | (2006.01) | |
| *B29C 39/28* | (2006.01) | |
| *B29L 31/00* | (2006.01) | |

(52) U.S. Cl.
CPC .......... *B29C 48/277* (2019.02); *B29C 39/025* (2013.01); *B29C 39/123* (2013.01); *B29C 39/28* (2013.01); *B29C 48/17* (2019.02); *B29C 48/21* (2019.02); *B29L 2031/718* (2013.01); *B29L 2031/7184* (2013.01)

(58) Field of Classification Search
None
See application file for complete search history.

(56) References Cited

U.S. PATENT DOCUMENTS

| | | | |
|---|---|---|---|
| 3,192,933 A | 7/1965 | Prince | |
| 3,279,999 A | 10/1966 | Harrison | |
| 3,479,429 A | 11/1969 | Morshauser et al. | |
| 3,493,309 A | 2/1970 | Grisel | |
| 4,202,879 A | 5/1980 | Shelton | |
| 4,291,018 A | 9/1981 | Oeda et al. | |
| 4,743,443 A | 5/1988 | Pisani et al. | |
| 4,791,248 A * | 12/1988 | Oldenettel | H05K 1/056 174/265 |
| 5,160,689 A | 11/1992 | Kamen | |

(Continued)

*Primary Examiner* — Timothy Kennedy
*Assistant Examiner* — Olukorede Esan
(74) *Attorney, Agent, or Firm* — Andrus Intellectual Property Law, LLP

(57) ABSTRACT

A method for manufacturing a cosmetic stick having at least two different colored portions includes inserting a pin into at least one mold cavity of a mold body, filling the mold cavity containing the pin with a first cosmetic material of a first color, and then recovering the excess first cosmetic material from a top surface of the mold body. The pin is removed from the mold cavity leaving a void in the mold cavity, and a guard plate is placed over the top surface of the mold body, the guard plate having a hole over the mold cavity. The void in the mold cavity is filled with a second cosmetic material, the second cosmetic material being a second color that is different than the first color. The excess second cosmetic material is then recovered from a top surface of the guard plate.

20 Claims, 8 Drawing Sheets

(56) References Cited

U.S. PATENT DOCUMENTS

| | | | |
|---|---|---|---|
| 5,780,018 A * | 7/1998 | Collins | A61K 8/0241 424/DIG. 5 |
| 6,648,026 B2 | 11/2003 | Look et al. | |
| 6,695,510 B1 | 2/2004 | Look et al. | |
| 6,955,489 B2 | 10/2005 | Look et al. | |
| 7,073,965 B2 | 7/2006 | Look et al. | |
| 2002/0041788 A1 * | 4/2002 | Look | A61K 8/44 401/68 |
| 2002/0109262 A1 | 8/2002 | Grosz | |
| 2002/0127192 A1 | 9/2002 | Murphy et al. | |
| 2007/0224144 A1 * | 9/2007 | Lazzarini | B65B 1/24 424/70.1 |
| 2014/0345639 A1 | 11/2014 | Samain | |

* cited by examiner

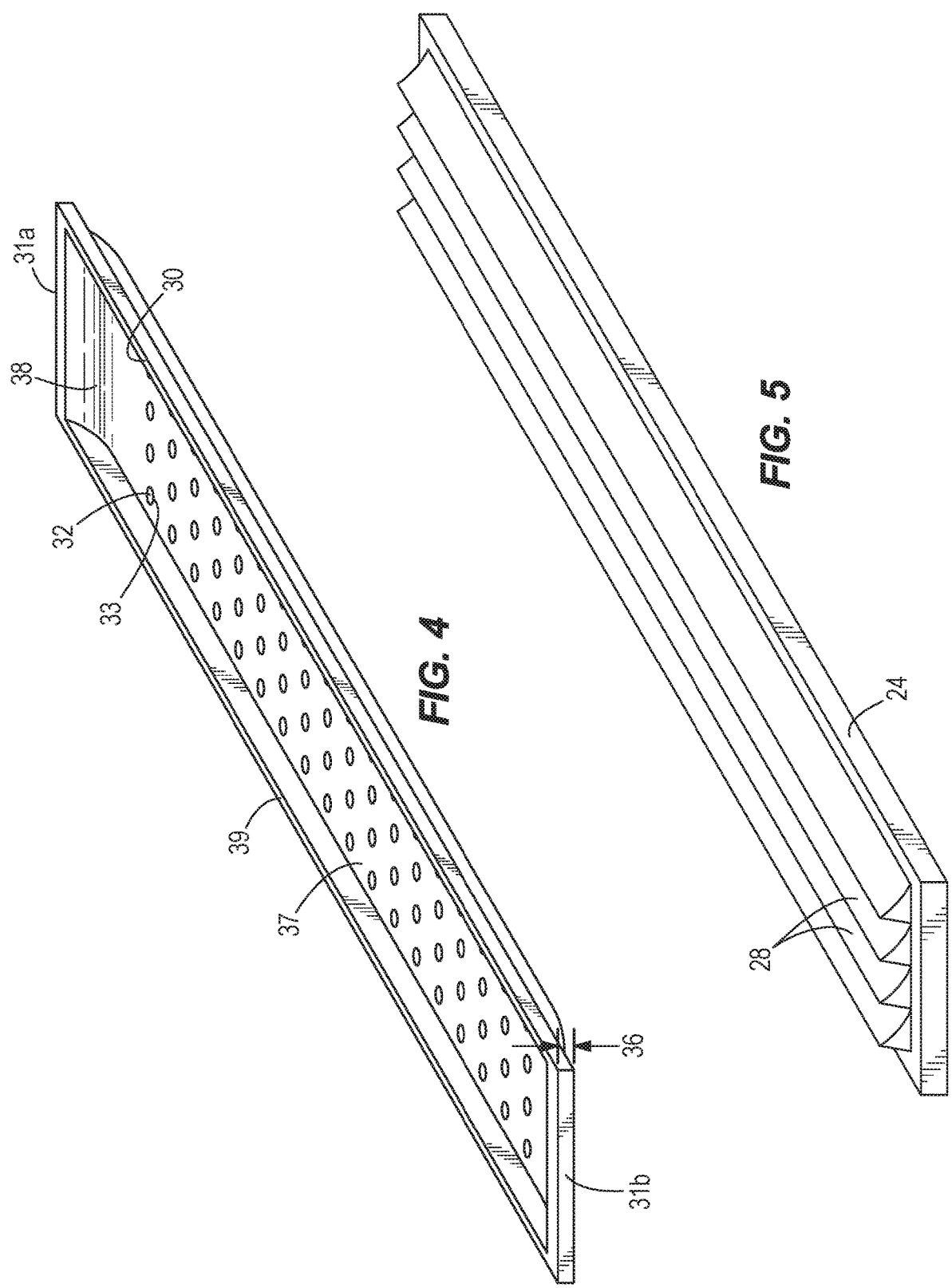

SYSTEM AND METHOD FOR MANUFACTURING A COSMETIC STICK

CROSS REFERENCE TO RELATED APPLICATION

This application is a divisional of U.S. patent application Ser. No. 15/231,230, filed Aug. 8, 2016, which is incorporated herein by reference.

FIELD

The present disclosure relates generally to cosmetic products in a stick form, such as a lipstick or a concealer stick, and more specifically to a system and method for manufacturing such a cos metic stick having at least two portions of different materials and/or composition that minimizes the amount of cosmetic material wasted in the manufacturing process.

BACKGROUND

Methods and systems have been developed for manufacturing multi-color cosmetic sticks, such as lipsticks, involving inserting two or more different cosmetic materials, such as two or more portions of different colors, into a mold. The following references are incorporated herein by reference in their entireties.

U.S. Pat. No. 4,291,018 discloses a lipstick having a construction of the core-sheath type which comprises two different compositions A and B arranged in core-sheath relationship, the composition A consisting essentially of a homogeneous mixture of from 53 to 85% by weight of a low-viscosity oily ingredient having a viscosity of less than approximately 80 centipoises at 36 degrees Celsius and from 15 to 47% by weight of a waxy ingredient having the form of a solid at 36 degrees Celsius and the composition B consisting essentially of a homogeneous mixture of from 40 to 90% by weight of a viscous oily ingredient having a viscosity of at least 200 centipoises at 36 degrees Celsius and from 10 to 60% by weight of said waxy ingredient. When applied to the lips, this lipstick causes no tacky or disagreeable sensation, spreads well with a soft feel and a light touch, adheres evenly to the lips and gives protection thereto, and provides a good and beautiful gloss, clarity, hue, and color development.

U.S. Pat. No. 7,073,965 discloses a multi-composition stick product, such as a lip balm, sun screen, deodorant, or glue stick. The multi-composition stick product including a stick composition molded in the container so as to contact the walls thereof and be advanceable or ejected therefrom. The stick composition includes a first composition and a second composition. The first and second compositions differ in at least one component, such as a medicament, colorant, fragrance, flavorant, sunscreen, preservative, conditioner, moisturizer, emollient, or surfactant. Furthermore the first and second compositions are arranged in a predetermined non-random pattern that is reproducible. Also described is the method and apparatus for manufacturing the multi-composition stick product.

U.S. Pat. No. 4,743,443 discloses a tri-color or alternating bi-color lipstick and method of molding the same is disclosed. The lipstick is formed using a known book-type mold. The color divisions are achieved by using a removable insert. One insert is used to form the middle section. Another insert is a solid plate and is used to prevent lipstick product from entering the middle section while the outer sections are being filled. In use, the lipstick is axially rotated by the user to present the desired color to the lips. In serial or simultaneous fashion, more than one color may be applied to permit blending.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

A method for manufacturing a cosmetic stick having at least two differently colored portions includes inserting a pin into at least one mold cavity of a mold body, filling the mold cavity containing the pin with a first cosmetic material of a first color, and then recovering the excess first cosmetic material from a top surface of the mold body. The pin is removed from the mold cavity leaving a void in the mold cavity, and a guard plate is placed over the top surface of the mold body, the guard plate having a hole over the mold cavity. The void in the mold cavity is filled with a second cosmetic material, the second cosmetic material being a second color that is different than the first color. The excess second cosmetic material is then recovered from a top surface of the guard plate.

One embodiment of a system for manufacturing a cosmetic stick having at least two differently colored portions includes a mold body having at least one mold cavity and a pin plate removably placeable on the mold body and having at least one pin insertable into the mold cavity. The pin plate and mold body are configured to allow filling a portion of the mold cavity not occupied by the pin with a first cosmetic material and then removing the pin to create a void in the first cosmetic material in the mold cavity. The system further includes a guard plate removably placeable on the mold body, the guard having a hole that allows a second cosmetic material to be inserted into the void. The guard plate further has a top surface that enables recovery of excess second cosmetic material without contamination by the first cosmetic material.

Another embodiment of a system for manufacturing a cosmetic stick includes a mold body having at least one mold cavity and a first cosmetic material of a first color inserted into the mold cavity. The system further includes a second cosmetic material of a second color inserted in the mold cavity adjacently positioned to the first cosmetic material. A guard plate is removably placed on a top surface of the mold body after the first cosmetic material is inserted into the mold cavity. The guard plate has a flat top surface enabling recovery of excess second cosmetic material without contamination by the first cosmetic material.

Various other features, objects, and advantages of the invention will be made apparent from the following description taken together with the drawings.

BRIEF DESCRIPTION OF THE DRAWINGS

The present disclosure is described with reference to the following Figures.

FIG. 4 depicts a guard plate portion of a system for manufacturing a cosmetic stick.

FIG. 5 depicts a bottom plate portion of a system for manufacturing a cosmetic stick.

DETAILED DESCRIPTION

Figure 1:
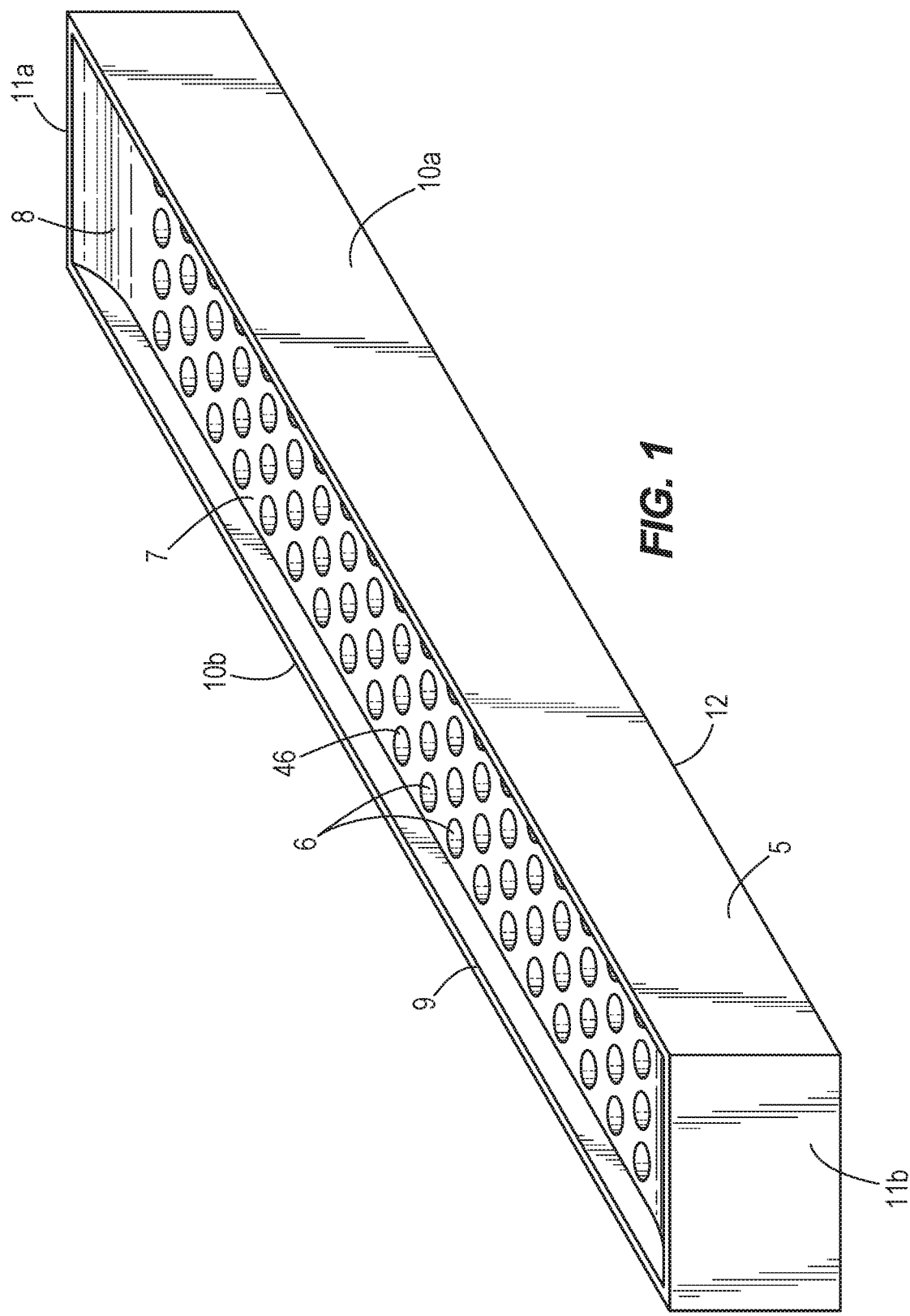
FIG. 1 depicts one embodiment of a mold body portion of a system for manufacturing a cosmetic stick.

A long standing problem in the manufacture of multi-material, molded cosmetic products, such as a cosmetic stick having portions comprised of differently colored cosmetic materials, is a high degree of waste during the manufacture process because excess materials from later manufacturing stages cannot be recycled due to contamination (mixing) with the materials from earlier manufacturing stages. More specifically, the recovered excess of materials inserted secondly or thirdly into a mold cannot be reused because they contain some amount of the earlier inserted materials. This leads to significant waste because the contaminated excess cannot be reused. This adds significant expense to the manufacture cost. For instance, in many cosmetic stick manufacturing applications the waste due to unusable contaminated excess is 70% or more, and in some applications exceeds 100%.

Various solutions to this problem have been devised, yet have been inadequate. For example, U.S. Pat. No. 7,073,965 is directed to this problem of waste in multi-material molded cosmetic manufacture and discloses a solution having a heated plate metal scraper that trails the material dispensing nozzle in order to push each cosmetic material forward and reduce the excess amount of composition. However, this and other prior art solutions are undesirable because they are complicated, expensive, prone to maintenance issues, and do not sufficiently reduce the waste due to contaminated excess.

In light of the above-mentioned long standing problem and need in the relevant cosmetic manufacture art, the present inventors have endeavored to develop and have developed a system and method of manufacturing a cosmetic stick having at least two different materials, such as two differently colored portions, wherein waste due to contamination of excess material is significantly reduced. The disclosed system and method employs one or more guard plates 30 removably placed on a mold body 5, wherein a guard plate 30 is provided for each additional cosmetic material added after the first cosmetic material is inserted into the one or more mold cavities 6 in the mold body 5.

In one embodiment depicted in the figures, a system 1 for manufacturing a cosmetic stick and an associated method include a mold body 5 including one or more mold cavities 6, and a pin 16 inserted into the mold cavity 6 while the mold cavity is filled with a first cosmetic material 42. The pin 16 is then removed, leaving a void in the first cosmetic material within the mold cavity 6. The void is then filled with a second cosmetic material 45, creating a multi-material cosmetic stick.

In applicant's inventive method and system, excess material is recovered after each filling stage—e.g., after filling the mold cavity 6 with the first cosmetic material 42 and after filling the mold cavity 6 with the second cosmetic material 45—and the excess of each material comprised in the cosmetic stick is recovered without being contaminated by the prior-inserted materials. FIG. 1 depicts one embodiment of a mold body 5 of the system 1 for manufacturing a cosmetic stick. The mold body 5 includes multiple mold cavities 6, each of which are filled with heated cosmetic material that cools in the molded cavity and then is removed as a cosmetic stick. In the depicted embodiment, each mold cavity 6 is generally cylindrical in shape, having a circular cross-sectional area with a circumference 46. In other embodiments, the mold cavity 6 could be any shape, such as having a square or triangular cross-section, or the like. The exemplary mold body 5 generally has an elongated rectangular shape, but in other embodiments could be any shape, and also could be any size. The depicted embodiment has a first longitudinal side 10a and a second longitudinal side 10b, each running the length of the rectangular mold body 5 between a first end 11a and a second end 11b. In the depicted embodiment, the mold body 5 has a side lip 9 running along each longitudinal side 10a and 10b. A ramped edge 8 extends from each end 11a and 11b of the mold body.

Figure 2:
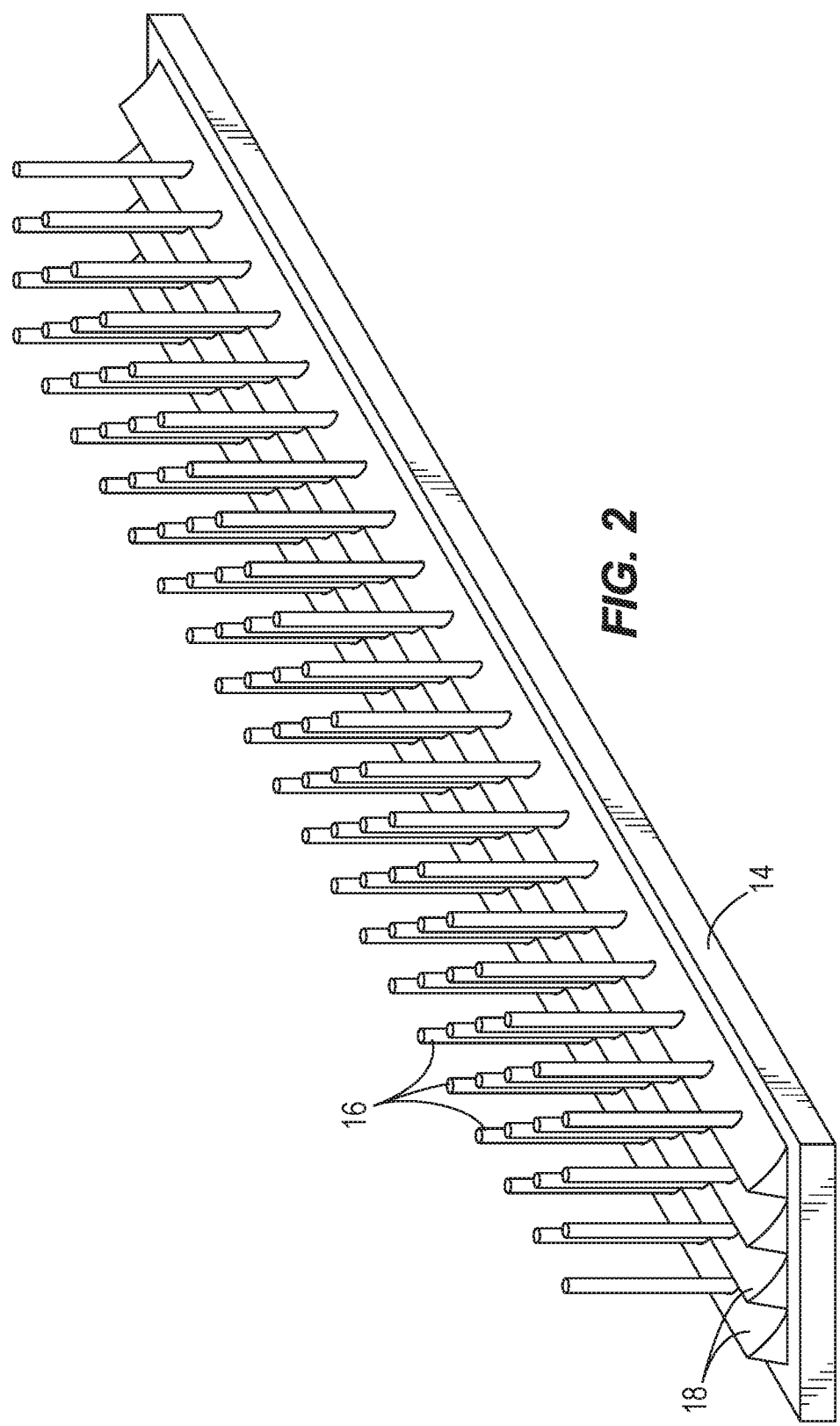
FIG. 2 depicts one embodiment of a pin plate portion of a system for manufacturing a cosmetic stick.

FIG. 2 depicts a pin plate 14 having pins 16 extending therefrom. More specifically, the pin plate 14 is configured to be removably connected to the mold body 5 so that each pin 16 is inserted into one of the mold cavities 6 of the mold body. In the depicted embodiment, the pin plate 14 is connected to the bottom side 12 of the mold body 5 such that the pins 16 extend upwards along the length of the mold cavities 6. In the depicted embodiment, the pin plate 14 has multiple sloped base portions 18, each aligning with a column of mold cavities 6 and forming a bottom portion of the mold cavities 6. The sloped base portions 18 form a slanted end on the cosmetic stick, such as for molding a lipstick. In other embodiments, the sloped base portion 18 may have another shape, such as curved base portions to form a curved end of the cosmetic stick. In other embodiments, the sloped base portions 18 may be eliminated completely, forming a flat end to the cosmetic stick.

Figure 3:
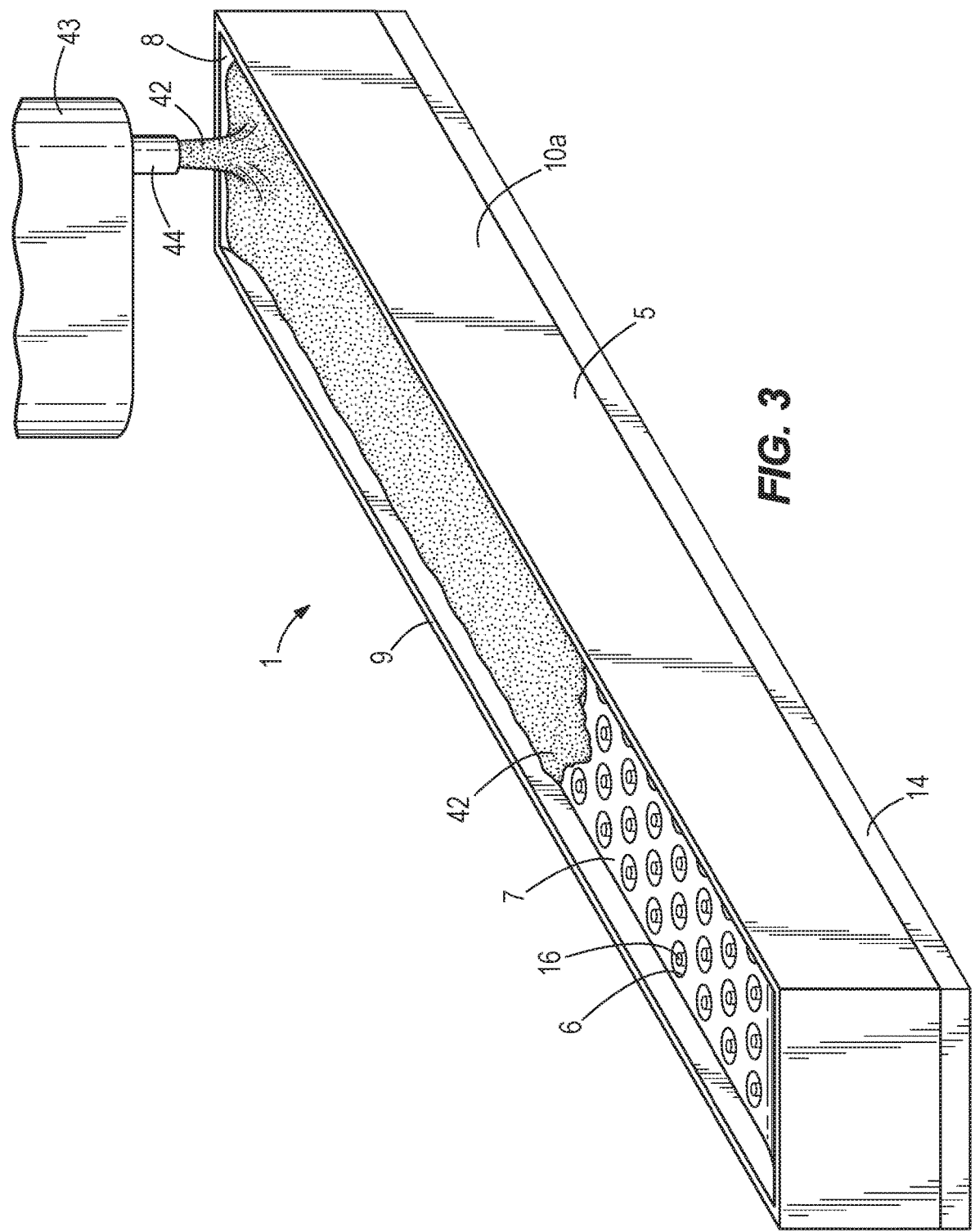
FIG. 3 depicts the pin plate of FIG. 2 connected the mold body of FIG. 1 in an exemplary system and method for manufacturing a cosmetic stick.

A first cosmetic material is poured over the top surface 7 of the mold body 5 when the pin plate 14 is connected to the mold body 5 and the pins 16 are inserted into the mold cavities 6. The cosmetic material is heated, and thus flows as a liquid when poured over the top surface 7 of the mold body 5. As depicted in FIG. 3, a first cosmetic material 42 may be contained in a bulk supply 43 that heats the first cosmetic material 42 so that it liquefies and can be dispensed from nozzle 44. The first cosmetic material 42 may be received on the ramped edge 8 of the top surface 7, causing it to flow across the top surface 7 and fill all of the mold cavities 6 of the mold body 5. The side lips 9 on either longitudinal side 10a and 10b of the mold body 5 retain the first cosmetic material in the area of the top surface 7 having the mold cavities 6, and thus forcing the melted first cosmetic material 42 to flow into and fill all of the mold cavities 6.

Once all of the mold cavities 6 containing the pins 16 have been filled with the first cosmetic material 42, the first cosmetic material 42 is cooled and solidifies within the mold body 5. Once the cooling process is complete, the pin plate 14 is separated from the mold body 5 removing the pins 16 from the mold cavities 6. Accordingly, a void is left in the first cosmetic material filling the mold cavity, which is the shape and size of the pin. In the depicted embodiment, the pins 16 are cylindrical and situated in the center of each mold cavity 6, and thus the void would be a cylinder positioned in the center of the mold cavity. In other embodiments, the pin 16 may be any shape and may be positioned anywhere within the mold cavity 6. For example, the pin 16 may be a half cylinder occupying half of the mold cavity.

Since the first cosmetic material 42 must flow across the length of the mold body 5 in order to fill all of the mold cavities 6, a significant amount of excess remains on the top surface of the mold body 5 once all of the cavities 6 are filled. In the depicted embodiment, the excess cosmetic material can be recovered from the top surface 7 of the mold body 5, such as by scraping the excess first cosmetic material 42 from the top surface 7. Accordingly, the top surface 7 of the mold body 5 is substantially flat, or smooth, so that the first cosmetic material 42 can be scraped off of the top surface 7. The recovered excess first cosmetic material 42 may then be placed back into the bulk supply 43 and reheated so that it may be reused. In the depicted embodiment, the system 1 is configured so that the ends of the pins 16 are even with the top surface 7 of the mold body 5—i.e., so that the void extends the full length of the mold cavity 6 yet the pins 16 do not inhibit progression of a scraper across the top surface 7 of the mold body 5.

Once the excess first cosmetic material is recovered and the pins are removed from the mold cavities 6, the mold body 5 is prepared so that the voids can be filled with a second cosmetic material. Specifically, a guard plate 30 is placed over the top surface 7 of the mold body 5, an exemplary embodiment of which is shown in FIG. 4. A bottom plate 24 is placed on the bottom side 12 where the pin plate 14 used to be. FIG. 5 provides an exemplary bottom plate 24 having sloped base portions 28 that are the same shape and size as the sloped base portions 18 of the pin plate 14. Accordingly, when the pin plate 14 is removed from the mold body 5 and replaced by the bottom plate 24, the bottom plate 24 is shaped to match the molded first cosmetic material 42 that is already in the mold cavities 6.

The guard plate 30 has holes 32 that align with the mold cavities 6 so that the holes 32 are over the mold cavities 6 when the guard plate 30 is connected to the top surface 7 of the mold body 5. The guard plate 30 follows the top surface 7 of the mold body 5 so that little or not space exists between the top surface 7 of the mold body 5 and the bottom of the guard plate 30. Thereby, no subsequently inserted cosmetic material is permitted to build up between the top surface 7 of the mold body 5 and the bottom of the guard plate 30.

The guard plate 30 has a top surface 37 that performs similarly as described above to receive a second cosmetic material that will fill the voids in the mold cavities 6 formed by removal of the pins 16. Specifically, a second cosmetic material 45 is poured over the top surface 37 of the guard plate 30, such as onto the sloped edge 38 thereof. Side lips 31a, 31b retain the second cosmetic material 45 on the top surface 37, and the second cosmetic material flows through the holes 32 in order to fill the voids in the mold cavities 6. Preferably, the holes 32 have a circumference 33 that is the same size or smaller than the circumference 46 of each mold cavity 6. In the depicted embodiment, the circumference 33 of each hole 32 is the same size as the circumference 46 of each mold cavity 6, and the holes 32 align with the mold cavities 6 to form one continuous cylindrical shape. In other embodiments, the holes 32 may be sized to align with the void left by the pins, and thus may be smaller than the cross-sectional area of the mold cavities 6. Such an embodiment may maximize the amount of second cosmetic material recoverable from the top surface 37 of the guard plate 30. However, one of skill in the art will understand in light of the disclosure that the holes 32 may be any size and at any location that allows the second cosmetic material 45 to fill the voids in the mold cavities 6 left by removal of the pins 16.

Figure 6:
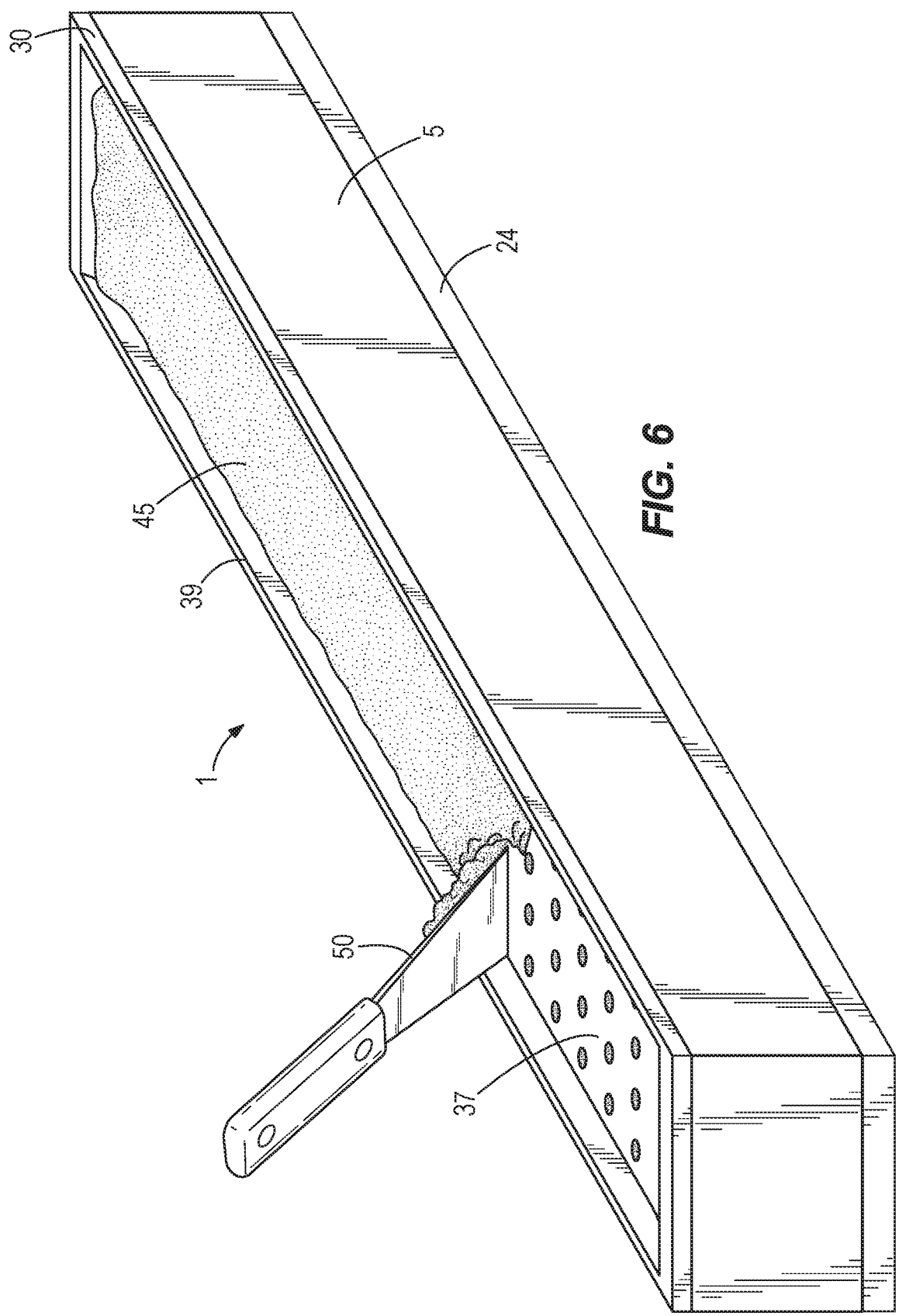
FIG. 6 depicts the guard plate of FIG. 4 and the bottom plate of FIG. 5 assembled to the mold body of FIG. 1 in an exemplary embodiment of a method and system for manufacturing a cosmetic stick.

FIG. 6 exemplifies recovery of the second cosmetic material 45. A scraper 50 scrapes the top surface 37 of the guard plate 30 to recover the excess second cosmetic material 45 solidified on the guard plate 30. Thus, the top surface 37 of the guard plate 30 is substantially flat, or smooth, as described above with respect to the top surface 7 of the mold body 5, so that the second cosmetic material 45 can be scraped from the top of the guard plate 30. Scraper 50 may be comprised of any material, such as a hard plastic or metal. Accordingly, the guard plate 30 provides a separation between the first cosmetic material 42 on the top surface 7 of the mold body 5 and the recovery surface for the second cosmetic material 45, thereby avoiding contamination in the recovered second cosmetic material 45. Accordingly, the second cosmetic material 45 recovered from the top of the guard plate 30 can be reused, such as returned to a bulk supply of the second cosmetic material. The guard plate 30 has a thickness 36 sufficient to provide such separation in order to prevent contamination of the second cosmetic material 45 by the first cosmetic material 42. In other words, the guard plate 30 must be thick enough such that unrecovered excess of the first cosmetic material 42 on the top surface 7 of the mold body 5 does not reach the level of the top surface 37 of the guard plate 30. In one embodiment, the guard plate may have a thickness of at least ⅛ of an inch. In other embodiments, the guard plate 30 may have a thickness 36 larger than ⅛ of an inch. However, in order to minimize the amount of excess second cosmetic material that is not recoverable, it is desirable to minimize the thickness 36 of the guard plate 30 to the minimum thickness that provides sufficient isolation between the first cosmetic material 42 and the second cosmetic material 45.

Once the second cosmetic material 45 is scraped or otherwise recovered from the top surface 37 of the guard plate 30, the guard plate 30 is removed from the mold body 5. Small amounts of the second cosmetic material 45 remain in the place of the holes 32 of the guard plate 30. That remaining second cosmetic material 45 is contaminated with first cosmetic material 42, and thus the remaining second cosmetic material 45 or first cosmetic material 42 that is removed from the top of the mold body 5 cannot be reused. The remaining first and second cosmetic materials 42 and 45 may be removed similarly as the recovered materials—i.e., by scraping the remaining material from the top surface 7 of the mold body 5 and then dispensed of. Once the cosmetic materials are sufficiently solidified in the mold cavities 6, the bottom plate 24 may be removed and the cosmetic material removed from the mold body 5 as formed cosmetic sticks—such as lipsticks, concealer sticks, blush sticks, or any other molded cosmetic product—which may then proceed to further packaging steps.

The elements of the system 1 for manufacturing a cosmetic stick, including the mold body 5, pin plate 14, bottom plate 24, and guard plate 30, may be comprised of any hard material that is sufficiently temperature resistant to withstand heating and cooling of the cosmetic materials without significant deformation or damage, such as metal.

Figure 7A:
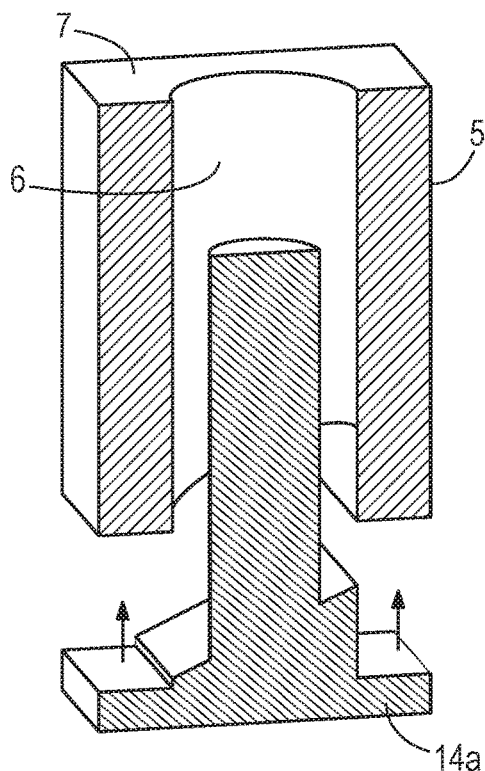
FIGS. 7A-7J depict another exemplary embodiment of a method and system for manufacturing a cosmetic stick.
Figure 7B:
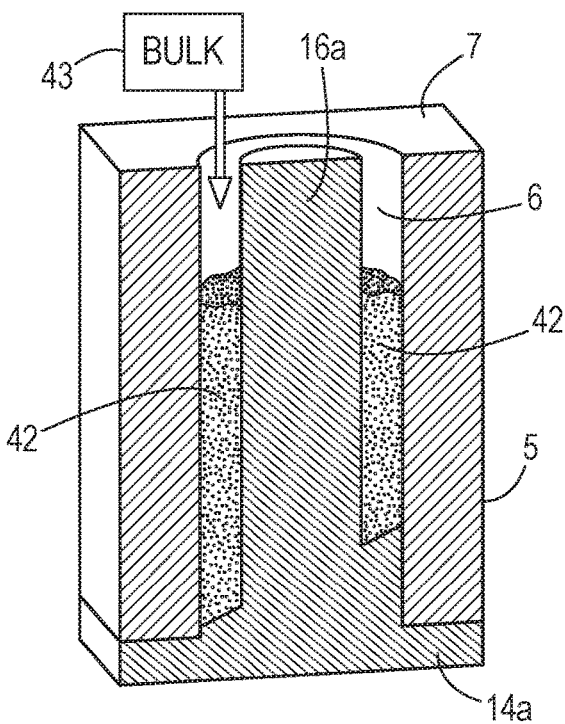
Figure 7C:
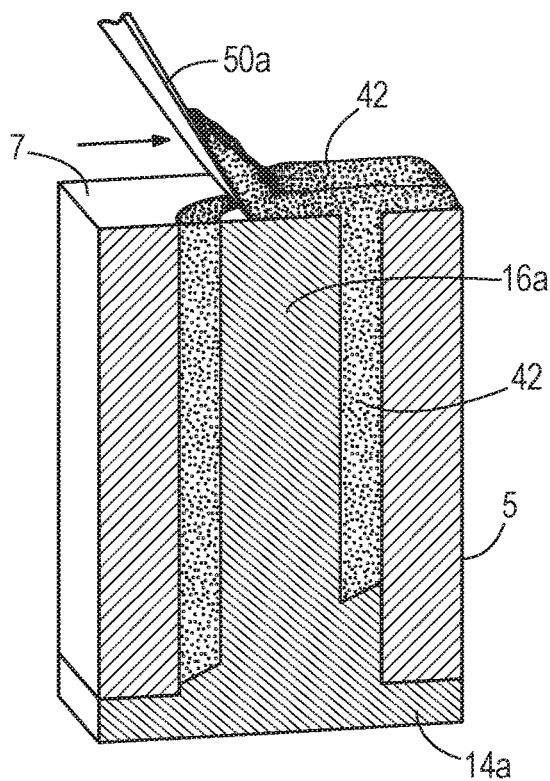
Figure 7D:
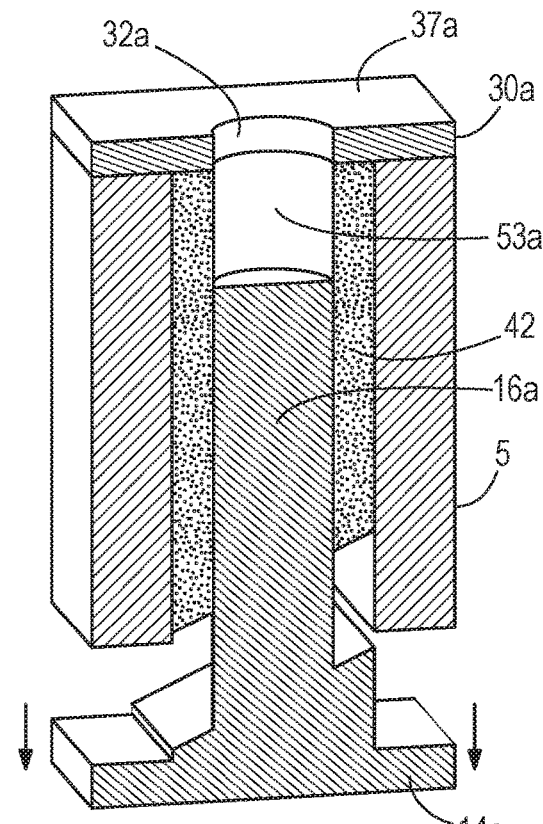
Figure 7E:
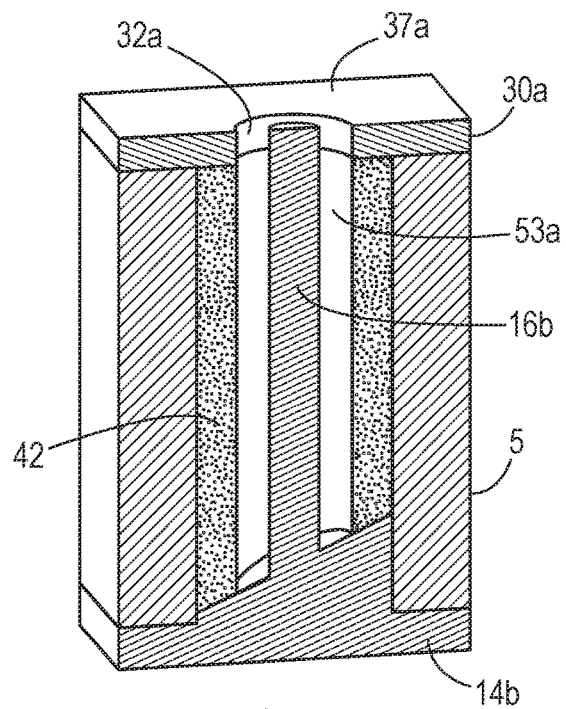
Figure 7F:
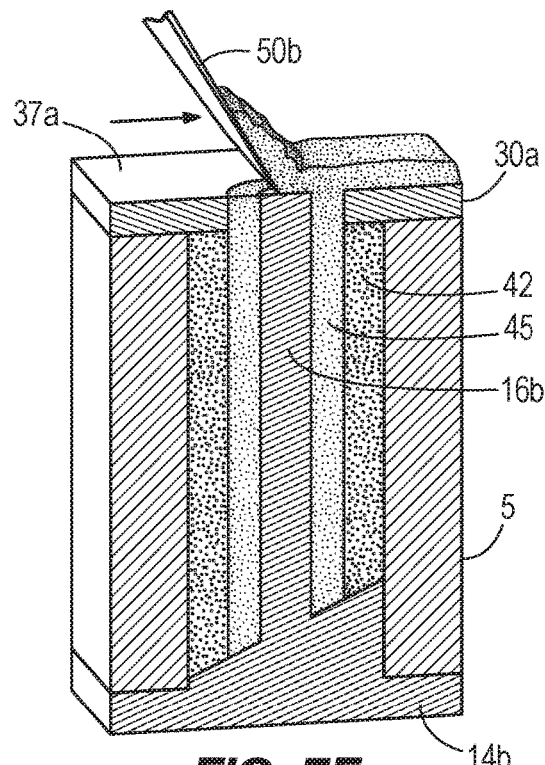
Figure 7G:
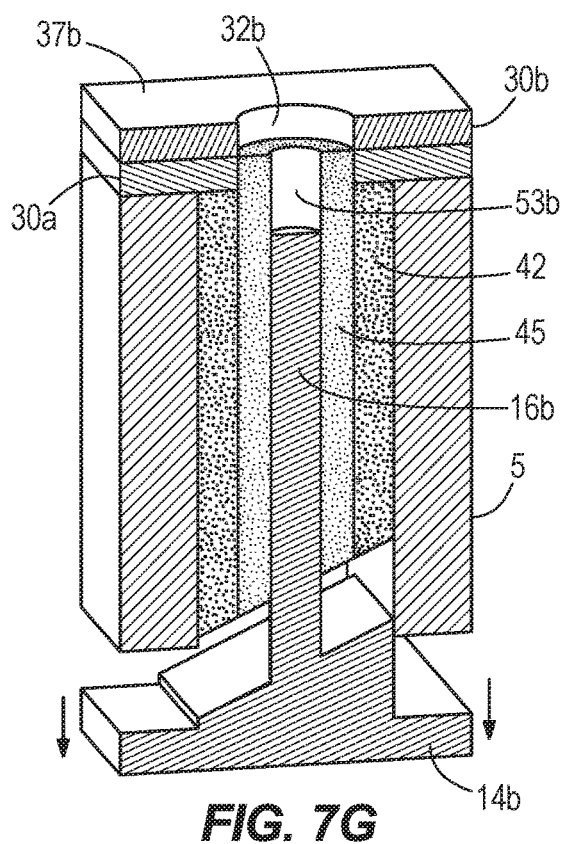
Figure 7H:
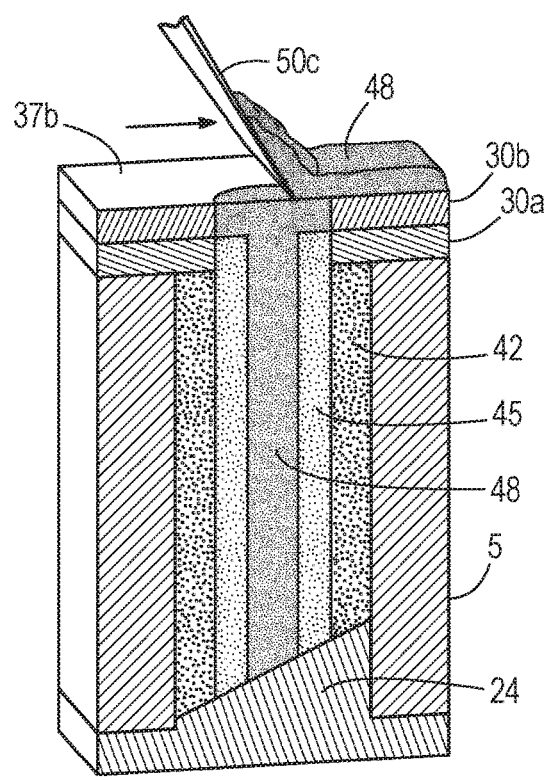
Figure 7I:
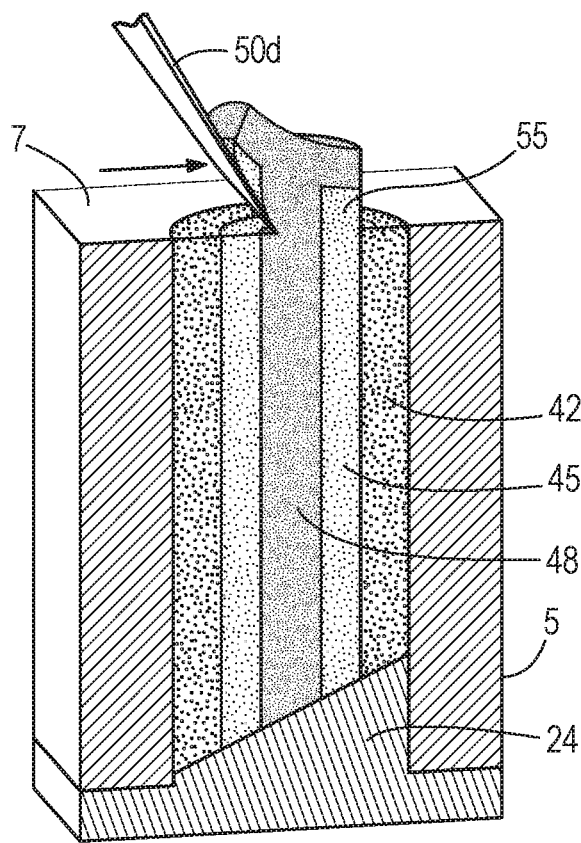
Figure 7J:
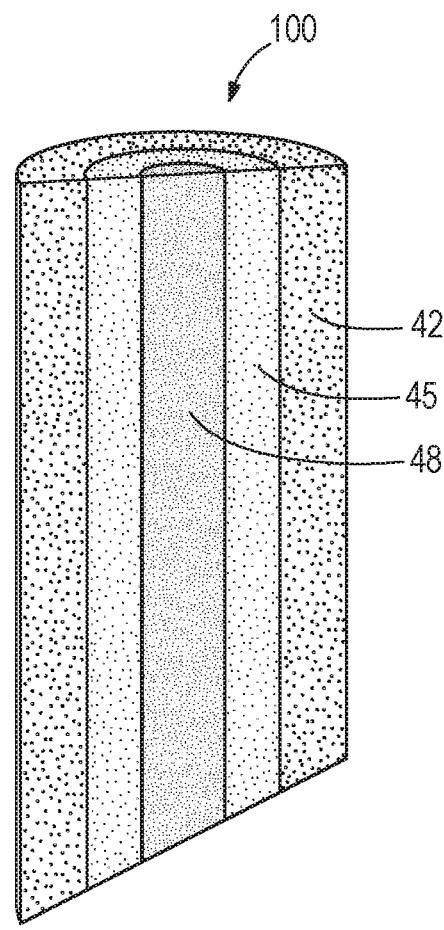

FIGS. 7A-7J depict one exemplary embodiment of a method and system for manufacturing a cosmetic stick 100 having at least two differently colored portions, and in this embodiment having three differently colored portions. The FIGS. 7A-7I depict a cross-sectional view of a mold cavity 6 during the manufacture process. FIG. 7J depicts a cross-sectional view of a finalized cosmetic stick 100 having three differently colored portions, including a first cosmetic material 42, a second cosmetic material 45, and a third cosmetic material 48, each cosmetic material 42, 45, 48 being a different color from the others. In another embodiment, the outer, first cosmetic material 42 and the inner, third cosmetic material 48 may be the same color, with the second cosmetic material 45 being a different, second color. The cosmetic materials 42, 45, 48 may be of the same or different compositions, as is described above.

FIG. 7A depicts a cross-section of a mold body 5 containing a mold cavity 6 with top surface 7. FIG. 7B depicts a first pin plate 14a having a first pin 16a inserted into the mold cavity 6, and a first cosmetic material 42 being dispensed from a first bulk supply 43 into the mold cavity 6. In FIG. 7C, the first cosmetic material 42 is being scraped from the top surface 7 of the mold body 5 by a first scraper 50a. In FIG. 7D, the first pin plate 14a and first pin 16a have been removed, leaving a first void 53a in the first cosmetic material 42. FIG. 7D also depicts a first guard plate 30a on top of the top surface 7 of the mold body 5. In the depicted embodiment, the first guard plate 30a has a top surface 37a and a hole 32a. In the depicted embodiment, the hole 32a in the first guard plate 30a is sized to have a circumference approximately the same size as a circumference of the first void 53a and to align directly above the first void 53a to allow a second cosmetic material 45 to enter the first void 53a.

As depicted in FIG. 7E, a second pin plate 14b having a second pin 16b is connected to the mold body 5 and the pin 16b is inserted into the first void 53a. The second pin 16b has a smaller volume than the first pin 16a, and thus does not fill the first void 53a. As depicted in FIG. 7F, a second cosmetic material 45 fills the first void 53a around the second pin 16b. Excess of the second cosmetic material 45 is scraped from the top surface 37a of the first guard plate 30a with scraper 50b. As depicted in FIG. 7G, a second guard plate 30b is then placed on top of the top surface of the first guard plate 30a after removal of the excess second cosmetic material 45. The second pin plate 14b and second pin 16b have been removed, leaving a second, smaller void 53b. A bottom plate 24 is connected to the mold body 5 and forms the bottom portion of the mold cavity, including of the smaller void 53b. A third cosmetic material 48 is then poured over the top surface 37b of the second guard plate 30b and flows through the hole 32b in the second guard plate 30b to fill the smaller void 53b. The excess third cosmetic material 48 is recovered from the top surface 37b of the second guard plate 30b by scraper 50c.

FIG. 7I depicts that the second guard plate 30b and the first guard plate 30a are removed from the mold body 5 leaving remaining cosmetic material 55, which is a mixture of the first, second, and third cosmetic materials 42, 45, and 48. The remaining cosmetic materials 55 are scraped from the top surface 7 of the mold body 5, such as by scraper 50d. The cosmetic stick 100 is then removed from the mold cavity 6, depicted in FIG. 7J, and can then proceed to further manufacturing steps, such as insertion into an appropriate cosmetic dispenser or container.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for manufacturing a cosmetic stick having at least two different cosmetic materials, the system comprising:
    a mold body having a mold cavity;
    a pin plate removably placeable on the mold body and having at least one pin insertable into the mold cavity, the pin plate and mold body configured to allow filling a portion of the mold cavity not occupied by the pin with a first cosmetic material and then removing the pin to create a void in the first cosmetic material in the mold cavity; and
    a guard plate removably placeable on the mold body, the guard plate having a hole that allows a second cosmetic material to be inserted through the hole and into the void and a top surface that enables recovery of excess second cosmetic material without contamination by the first cosmetic material.

2. The system of claim 1, wherein the hole in the guard plate is positioned over the void.

3. The system of claim 2, wherein the hole in the guard plate is sized to align with the mold cavity.

4. The system of claim 3, wherein at least a portion of the mold cavity is cylindrical, and the hole in the guard plate is a circle having the same circumference as the cylindrical portion of the mold cavity and aligning with the mold cavity.

5. The system of claim 1, wherein the hole in the guard plate has a circumference that is smaller than a circumference of the mold cavity.

6. The system of claim 1, wherein the mold body has a top surface configured to allow recovery of excess first cosmetic material, and wherein the guard plate is configured to be placed over the top surface of the mold body after recovery of the excess first cosmetic material.

7. The system of claim 6, wherein the pin plate is removably placeable on a bottom surface of the mold body.

8. The system of claim 7, further comprising at least one bottom plate removably placeable over a bottom surface of the mold body after removal of the pin plate and providing a bottom surface for each of the one or more mold cavities.

9. A system for manufacturing a cosmetic stick, the system comprising:
    a mold body having a mold cavity configured to receive a first cosmetic material of a first color inserted in the mold cavity and a second cosmetic material of a second color inserted in the mold cavity after the first cosmetic material and adjacently positioned to the first cosmetic material; and
    a guard plate configured to be removably placed on a top surface of the mold body after the first cosmetic material is inserted into the mold cavity and to facilitate insertion of the second cosmetic material into the mold cavity and to separate the second cosmetic material from the first cosmetic material on the top surface of the mold body such that excess second cosmetic material is recoverable without contamination by the first cosmetic material.

10. The system of claim 9, further comprising at least one pin configured to be removably placed in the at least one mold cavity so as to create a void in the first cosmetic material inside the mold cavity, wherein mold body has a top surface configured to allow recovery of excess first cosmetic material.

11. The system of claim 1, wherein the mold body includes a plurality of mold cavities, the pin plate includes a plurality of pins configured such that at least one pin is inserted into each mold cavity when the pin plate is placed on the mold body, and the guard plate includes a plurality of holes configured such that each hole is above at least one of the plurality of mold cavities when the guard plate is placed on the mold body.

12. The system of claim 9, wherein the guard plate is a rigid body comprising at least one hole configured to facilitate insertion of the second cosmetic material into the mold cavity and configured such that excess of the second cosmetic material can be scraped from a top of the guard plate.

13. The system of claim 9, wherein the mold body includes a plurality of mold cavities, the pin plate includes a plurality of pins configured such that at least one pin is inserted into each mold cavity when the pin plate is placed on the mold body, and the guard plate includes a plurality of holes configured such that each hole is above at least one of the plurality of mold cavities when the guard plate is placed on the mold body.

14. A system for manufacturing a cosmetic stick having at least two different cosmetic materials, the system comprising:
a mold body having a plurality of mold cavities;
a pin plate configured to be removably placed on the mold body and having a plurality of pins configured such that at least one pin is inserted into each mold cavity when the pin plate is placed on the mold body;
wherein the pin plate and mold body are configured to allow filling a portion of each mold cavity not occupied by the at least one pin with a first cosmetic material and then removing the at least one pin to create at least one void in the first cosmetic material in each mold cavity; and
a guard plate configured to be removably placed on the mold body, the guard plate having a plurality of holes configured to facilitate insertion of a second cosmetic material through the plurality of holes and into each of the at least one void in the first cosmetic material, wherein the guard plate is configured to separate the second cosmetic material from the first cosmetic material on the top surface of the mold body such that excess second cosmetic material is recoverable without contamination by the first cosmetic material.

15. The system of claim 14, wherein each of the plurality of holes in the guard plate is configured to align with one of the at least one void when the guard plate is placed on the mold body.

16. The system of claim 14, wherein each of the plurality of holes in the guard plate has a circumference that is equal to or smaller than a circumference of the mold cavity.

17. The system of claim 14, wherein the mold body has a smooth top surface configured to allow recovery of excess first cosmetic material, and wherein the guard plate is configured to be placed over the top surface of the mold body after recovery of the excess first cosmetic material.

18. The system of claim 14, wherein the pin plate is removably placeable on a bottom surface of the mold body.

19. The system of claim 18, further comprising a bottom plate removably placeable on a bottom surface of the mold body after removal of the pin plate and configured to provide a bottom surface for each of the one or more mold cavities.

20. The system of claim 14, wherein the guard plate is a rigid body comprising at least one hole configured to facilitate insertion of the second cosmetic material into the mold cavity and configured such that excess of the second cosmetic material can be scraped from a top of the guard plate.

* * * * *